United States Patent
Sun (10) Patent No.: US 11,229,590 B2
(45) Date of Patent: Jan. 25, 2022

(54) SUNSCREEN FORMULATION

(71) Applicant: Yimin Sun, Guangdong (CN)

(72) Inventor: Yimin Sun, Guangdong (CN)

( * ) Notice: Subject to any disclaimer, the term of this patent is extended or adjusted under 35 U.S.C. 154(b) by 361 days.

(21) Appl. No.: 16/494,342

(22) PCT Filed: Oct. 25, 2018

(86) PCT No.: PCT/CN2018/111881
§ 371 (c)(1),
(2) Date: Sep. 16, 2019

(87) PCT Pub. No.: WO2020/082296
PCT Pub. Date: Apr. 30, 2020

(65) Prior Publication Data
US 2021/0361548 A1 Nov. 25, 2021

(51) Int. Cl.
*A61K 8/365* (2006.01)
*A61Q 17/04* (2006.01)
*A61K 8/41* (2006.01)
*A61K 8/84* (2006.01)

(52) U.S. Cl.
CPC ............. *A61K 8/365* (2013.01); *A61K 8/41* (2013.01); *A61K 8/84* (2013.01); *A61Q 17/04* (2013.01); *A61K 2800/52* (2013.01); *A61K 2800/805* (2013.01)

(58) Field of Classification Search
None
See application file for complete search history.

(56) References Cited

U.S. PATENT DOCUMENTS 3,489,739 A   1/1970   Yanai et al.
5,877,204 A   3/1999   Davison et al.

FOREIGN PATENT DOCUMENTS

| CN | 1149866 A | * 5/1997 | ......... C07D 207/452 |
|---|---|---|---|
| CN | 1149866 A | 5/1997 | |
| CN | 106176319 A | 12/2016 | |
| EP | 0407932 A2 | 1/1991 | |
| WO | 2017136809 A1 | 8/2017 | |

OTHER PUBLICATIONS

English language translation of CN 1149866A. (Year: 1997).*
International Search Report and Written Opinion dated Jun. 27, 2019 for International Application No. PCT/CN2018/111881.
A.M.Calafat, L.Y.Wong, X.Ye, J.A.Reidy, L.L.Needham, Concentrations of the sunscreen agent benzophenone-3 in residents of the United States: National Health and nutrition Examination Survey 2003-2004, Environ. Health Perspect, 116(2008)893-897].

(Continued)

*Primary Examiner* — Dominic Lazaro
(74) *Attorney, Agent, or Firm* — Enshan Hong; MagStone Law, LLP (57) ABSTRACT

The present invention relates to the synthesis of new classes of sunscreen agents, the usage of such sunscreen agents in sunscreen formulations aiming at reduction of sunscreen agents' skin penetration, and a formulation technology using existing sunscreen agents aiming at reduction of sunscreen agents' skin penetration, therefore improving the bio-safety of the sunscreen products.

20 Claims, 3 Drawing Sheets

(56) References Cited

OTHER PUBLICATIONS

J.Bae, S.Kim, K.Kannan, G.M.Buck Louis, Couples' urinary concentrations of benzophenone-type ultraviolet filters and the secondary sex ratio, Sci. Total Environ. 543(2016)28-36.

C.Philippat, D.Bennett, A.M.Calafat, I.H.Picciotto, Exposure to select phthalates and phenols through use of personal care products among Californian Adults and their Children, Environ. Res. 140(2015)369-376.

N.R.Janjua, B.Mogensen, A.M.Andersson, J.H.Petersen, M.Henriksen, N.E.Skakeback, H.C.Wulf, Systemic Absorption of the Sunscreens Benzophenone-3, Octyl-Methoxycinnamate, and 3-(4-Methyl-Benzylidene) Camphor After Whole-Body Topical Application and Reproductive Hormone Levels in Humans, J. Invest.Dermatol., 123(2004) 57-61.

N.R.Janjua, B.Kongshoj, A.M.Andersson, H.C.Wulf, Sunscreens in human plasma and urine after repeated whole-body topical application, J. Eur. Dermatol. Venererol. 22(2008)456-461.

J.Rodriguez, H.I.Maibach, Percutaneous penetration and pharmacodynamics: Wash-in and wash-off of sunscreen and insect repellent, J.Dermatolog. Treatment, 27(2016)11-18.

B.Gulson, M.J.Mccall, D.M.Bowman, T.Pinheiro, A review of critical factors for assessing the dermal absorption of metal oxide nanoparticles from sunscreens applied to humans, and a research strategy to address current deficiencies Arch. Toxicol. 89(2015)1909-1930.

H.Gonzalez, Percutaneous absorption with emphasis on sunscreens, Photochem.Photobiol.Sci.,9(2010)482-488.

M.Schlumpf, K.Kypke, M.Wittassek, J.Angerer, H.Mascher, D.Mascher, C.Vökt, M.Birchler, W.Lichtensteiger, Exposure patterns of UV filters, fragrances, parabens, phthalates, organochlor pesticides, PBDEs, and PCBs in human milk: Correlation of UV filters with use of cosmetics, Chemosphere, 8(2010)1171-1183.

C.Philippat, M.Mortamais, C.Chevrier, C.Petit, A.M.Calafat, YEX, M.J.Silva, C.Brambilla, I.Pin, M.A.Charles, S. Cordier, R.Slama, Exposure to phthalates and phenols during pregnancy and offspring size at birth, Environ. Health Perspect, 120(2012)464-470.

* cited by examiner

SUNSCREEN FORMULATION

RELATED APPLICATIONS

This is a U.S. national stage of international application No. PCT/CN2018/111881 filed on Oct. 25, 2018, the entire content of which is incorporated herein as reference.

BACKGROUND OF INVENTION

1. Field of Invention

The present invention relates to synthesis of UV rays blockers and UV rays blocker sunscreen formulations with minimized skin penetration of UV rays blockers for protection of human skin from solar UV radiation.

2. Description of Prior Art

Since the 1930s, sunscreen has been used to prevent the maladies inflicted by the sun. There are several types of electromagnetic radiation emitted by the sun. Ultraviolet (UV) radiation is one type. Based on the characteristics of the UV rays interacted with human skin, it was divided into three bands based on wavelength: UVA rays (320-400 nm), UVB rays (290-320 nm) and UVC rays (100-290 nm). UVA radiation consists of 95% of all UV radiation emitted by sun and reaching the surface of the earth. UVA exposure usually remains constant throughout the day and the four seasons, whereas UVB exposure occurs more during the noon time and in the summer, and UVC is almost absorbed completely by $O_3$ never reaching the surface of the earth. UVA penetrates deeper into human skin and causes under-skin damage and under-skin cancers, while UVB causes pigmentation, sunburn, photocarcinogenesis. Two kinds of sunscreen agents (UV filters) are currently being used in sunscreens for minimization of these adverse effects: 1. organic (chemical) filters, e.g. avobenzone, oxybenzone (benzophenone-3, bp-3) or octocrylene, etc.; 2. inorganic (physical) filters, zinc oxide (ZnO) and titanium dioxide (TiO2). Organic filters absorb UV rays, while inorganic filters scatter/reflect UV rays to prevent UV rays' exposure. In order to cover the whole UV radiation band, UVA and UVB, sunscreens are usually comprised of more than one of these UV filters: organic, inorganic, or a combination of both types, which gives broad-spectrum of protection. Beyond its debatable efficiency, questions regarding the main ingredients of different sunscreens are being raised in recent years, in particular regarding potential toxicity these ingredients towards human health.

Since the first day of sunscreen usage in 1930s, the exposure to sunscreen agents has begun. Initially, the scope and frequency of the sunscreen usage among the human population were very limited. Therefore, the levels of UV filters found in human samples were usually low. However, for the last 20 years, the situation changed dramatically. In one epidemiological study conducted in 2003-2004, 2517 urine samples from United States general population were analyzed for the presence of oxybenzone (benzophenone-3, bp-3), as part of the 2003-2004 National Health and Nutrition Examination Survey [A. M. Calafat, L. Y. Wong, X. YE, J. A. Reidy, L. L. Needham, *Concentrations of the sunscreen agent benzophenone-3 in residents of the United States: National Health and nutrition Examination Survey* 2003-2004, Environ. Health Perspect, 116 (2008) 893-897]. Oxybenzone was detected in 97% of the all samples with mean concentration of 22.9 ng/ml and 95th percentile concentration of 1040 ng/ml. As the data indicates, the sunscreen agent occurrences are wide spread. Later on another study was carried out focusing on investigating correlation between couples' presence of urinary benzophenone-type UV filters and sex ratio of their offspring, the mean concentrations of these UV absorber compounds ranged from 0.05 ng/ml to 8.65 ng/ml, with bp-3 as the most predominant among the study population (samples collected between 2005 and 2009 in Michigan and Texas)[J. Bae, S. Kim, K. Kannan, G. M. Buck Louis, *Couples' urinary concentrations of benzophenone-type ultraviolet filters and the secondary sex ratio*, Sci. Total Environ. 543 (2016) 28-36]. In 2007-2009, a study conducted in California among female subjects revealed very surprising findings. About nine times higher than previously reported levels of oxybenzone (up to 13000 ng/ml, average around 200 ng/ml) were found in urine samples collected in 2007-2009 from Californian females, which is probably a result of specific demographics [C. Philippat, D. Bennett, A. M. Calafat, L. H. Picciotto, *Exposure to select phthalates and phenols through use of personal care products among Californian Adults and their Children*, Environ. Res. 140 (2015) 369-376]. Compared to the 2003-2004 study, the average oxybenzone concentration in urine sample increased more than 9 folds, from 22.9 ng/mL to 200 ng/mL. It was an alarming development.

The experimental studies confirmed substantial absorption and distribution of organic filters, whereas inorganic filters seem to penetrate the human skin in a minimal degree. When adults applied a sunscreen formulation containing 10% of oxybenzone, 4-methylbenzylidene camphor (4-MBC) and octyl methoxycinnamate (OMC) on a daily basis (2 mg/cm$^2$) for a week, the mean urine concentrations for these ingredients were 60, 5, 5 ng/ml for females and 140, 7, 8 ng/ml for males, respectively [19N. R. Janjua, B. Mogensen, A. M. Andersson, J. H. Petersen, M. Henriksen, N. E. Skakeback, H. C. Wulf. *Systemic Absorption of the Sunscreens Benzophenone-3, Octyl-Methoxycinnamate, and 3-(4-Methyl-Benzylidene) Camphor After Whole-Body Topical Application and Reproductive Hormone Levels in Humans*, J. Invest. Dermatol., 123 (2004) 57-61]. At the same time, maximum plasma concentrations for these ingredients, reached 3-4 h after application, were 200, 20, 10 ng/ml for females and 300, 20, 2 ng/ml for males, respectively. Similar findings were reported following a 4-day exposure to these ingredients, which were detectable in the plasma of human males and females merely 2 h following application [20 N. R. Janjua, B. Kongshoj, A. M. Andersson, H. C. Wulf, *Sunscreens in human plasma and urine after repeated whole-body topical application*, J. Eur. Dermatol. Venererol. 22 (2008) 456-461]. More data on human skin penetration and distribution of various UV filters, both organic and inorganic, can be found in recent reviews. [21 J. Rodriguez, H. L. Maibach, *Percutaneous penetration and pharmacodynamics: Wash-in and wash-off of sunscreen and insect repellent*, J. Dermatolog. Treatment, 27 (2016) 11-18: 22, B. Gulson, M. J. Mccall, D. M. Bowman, T. Pinheiro, *A review of critical factors for assessing the dermal absorption of metal oxide nanoparticles from sunscreens applied to humans, and a research strategy to address current deficiencies* Arch. Toxicol. 89 (2015) 1909-1930; 15, H. Gonzalez, *Percutaneous absorption with emphasis on sunscreens*, Photochem. Photobiol. Sci., 9 (2010) 482-488].

Of importance, some UV filters were also found in human milk samples. In a cohort study between 2004 and 2006, 54 human milk samples were analyzed. UV filters were detectable in 46 samples, and levels were positively correlated with the reported usage of UV filter products[23 M.

Schlumpf, K. Kypke, M. Wittassek, J. Angerer, H. Mascher, D. Mascher, C. Vökt, M. Birchler, W. Lichtensteiger, *Exposure patterns of UV filters, fragrances, parabens, phthalates, organochlor pesticides, PBDEs, and PCBs in human milk: Correlation of UV filters with use of cosmetics, Chemosphere*, 8 (2010) 1171-1183].

In other study, levels of bp-3 in maternal urinary samples taken in gestational weeks 6-30 were positively correlated with the overall weight and head circumference of the baby [24 C. Philippat, M. Mortamais, C. Chevrier, C. Petit, A. M. Calafat, YEX, M. J. Silva, C. Brambilla, I. Pin, M. A. Charles, S. Cordier, R. Slama, *Exposure to phthalates and phenols during pregnancy and offspring size at birth*, Environ. Health Perspect, 120 (2012) 464-470]. These reports raise concerns about potential prenatal exposure and developmental toxicity of UV filters.

Although all data has shown exposure to sunscreen agents through usage of sunscreen products is wide spread, very little research on improving the bio-safety of sunscreen products by reducing or completely eliminating such exposure has been reported.

SUMMARY OF THE INVENTION

The present invention provides a formulation to reduce or minimize or eliminate the skin penetration of sunscreen agents, therefore improving bio-safety of sunscreen products.

According to a first aspect of the present application, a sunscreen formulation comprises:
(1) an ionic complex that is formed between a compound A and an excipient B; and
(2) an aqueous based carrier for topical administration.

The compound A is a sunscreen compound in enol form or with an active acidic proton or derivatized with $-[CH_2]_n COOH$ or $-[CH_2]_n NH_2$, n=0-18.

The excipient B contains an amine functional group when the sunscreen compound is in enol form or with an active acidic proton or derivatized with $-[CH_2]_n COOH$, and contains a carboxyl functional group when the sunscreen compound A is derivatized with $-[CH_2]_n NH_2$.

The formulation is substantially free of the compound A in a free form.

The sunscreen formulation is homogeneously transparent, preferably an ointment or a viscus solution.

The formulation comprises preferably less than 20%, more preferably 10%, most preferably less than 5%, molar equivalent of the compound A in free form relative to the molar amount of the ionic complex.

The formulation is preferably free of a compound that is substantially detrimental to formation or existence of the ionic complex or the stability of the formulation. The compound that is substantially detrimental to formation or existence of the ionic complex or the stability of the formulation is another ionic compound that is not described above explicitly. The compound that is substantially detrimental to formation or existence of the ionic complex or the stability of the formulation may be an ionic surfactant.

The sunscreen compound to be derivatized with $[CH_2]_n COOH$ may be avobenzone, cinoxate, dioxybenzone, homosalate, octocrylene, octyl methoxycinnamate, octyl salicylate, oxybenzone, or a combination thereof, and the derivatized sunscreen compound has the following structure:

preferably (4-benzoyl-3-hydroxy-phenoxy)-acetic acid of the following formula:

The sunscreen compound to be derivatized with $-[CH_2]_n NH_2$ may be avobenzone, cinoxate, dioxybenzone, homosalate, octocrylene, octyl methoxycinnamate, octyl salicylate, oxybenzone, or a combination thereof, and the derivatized sunscreen compound has the following structure:

preferably (4-aminomethoxy-2-hydroxy-phenyl) phenylmethanone of the following formula:

The excipient B that contains the amine functional group may be spermidine, spermine, tris-(2-aminoethyl)amine, 1,1,1-tris(aminomethyl)ethane, cyclen, polyvinylamine, polyallylamine, polyethyleneimine, chitosan, or a combination thereof, preferably a branched polyethyleneimine with a molecular weight of 1000-50000.

The excipient B that contains the carboxyl function group may be oxalic acid, malonic acid, succinic acid, glutaric acid, adipic acid, citric acid, isocitric acid, propane-1,2,3-tricarboxylic acid, carboxymethyl cellulose, polyacrylic acid, hyaluronic acid, or a combination thereof, preferably glutaric acid or polyacrylic acid having a molecular weight of 1000-50000.

The sunscreen compound in enol form is preferably avobenzone.

The sunscreen compound with the active acidic proton is preferably oxybenzone, diethylamino hydroxybenzoyl hexyl benzoate, homosalatem, dioxybenzone, 2-ethylhexyl salicylate, sulisobenzone, or a combination thereof.

The carrier may be aqueous based chitosan, aqueous based hyaluronic acid, aqueous based PEG200, aqueous based PEG400, aqueous based PEG1500, or a combination thereof.

According to a second aspect of the present application, a method for protecting skin from ultraviolet radiation comprising applying the formulation described above to the skin in need thereof.

According to a third aspect of the present application, a method of making the formulation comprises:

dissolving the compound A in the carrier, reacting with no less than, preferably greater than 20%, stoichiometric amount of the excipient B, and blending to form the composition, preferably a homogeneously transparent composition, more preferably ointment or viscus solution, at a temperature range from 20° C. to 50° C.

The method may comprise, prior to the step of blending, a step of making the compound A by derivatizing the sunscreen compound with —[CH$_2$]$_n$COOH or —[CH$_2$]$_n$NH$_2$, n=0-18.

According to a fourth aspect of the present application, a (4-aminomethoxy-2-hydroxy-phenyl) phenyl-methanone of the following formula:

which may be used in the above formulation as a derivatized sunscreen compound, is provided.

DETAILED DESCRIPTION OF PREFERRED EMBODIMENTS OF THE INVENTION

The following embodiments are provided to illustrate, but not to limit the instant invention.

New organic sunscreen agents with specifically designed functions for formulation purposes were synthesized.

A formulation scheme of using sunscreen agents containing a carboxy group coupled with simple organic compounds, oligomers, or macromolecules which contains amine groups was developed. Such combination is to result in interaction between a carboxy group of a sunscreen agent and an amine group of an excipient molecule to reduce/eliminate skin penetration of the sun screen agent.

A formulation scheme of using sunscreen agents containing amine groups coupled with simple organic compounds, oligomers, or macromolecules containing carboxy group was developed. The ionic interaction between the amino groups of the sunscreen agent and the carboxy groups of the excipient molecules will reduce, minimize, or eliminate skin penetration of sunscreen agents.

A formulation scheme of utilizing amino-group-containing simple organic compounds, oligomers, or macromolecules to interact with enol form of sunscreen agent (avobenzone) or with the active acidic proton of sunscreen agents (oxybenzone, diethylamino hydroxybenzoyl hexyl benzoate, homosalate, dioxybenzone, 2-ethylhexyl salicylate, sulisobenzone), was developed to generate ionic interaction between the amino-group-containing simple organic compounds, oligomers, or macromolecules and sunscreen agents. Such combination is to minimize, reduce, or eliminate skin penetration of sunscreen agents by promoting the interaction between the sunscreen agents and NH$_2$ groups of the excipient.

The present inventor has made intensive research to develop new active sunscreen agents bearing specifically designed function groups and to develop formulation scheme which will reduce skin penetration of sunscreen agents or at best eliminate the skin penetration of sunscreen agents for the ultimate purposes of enhancing the bio-safety of sunscreen products.

Accordingly, it is an objective of this invention to provide a synthesis of sunscreen agents which bears a carboxyl function group specifically designed for formulation purpose.

It is another objective of this invention to provide a synthesis of sunscreen agents which bears an amine function group specifically designed for formulation purpose.

In one aspect of the present invention there is provided a formulation scheme using the enol form or an active acidic proton of the sunscreen agents chemically interacting with NH$_2$ groups of simple organic compounds, oligomers, or macromolecules to reduce skin penetration of sunscreen agents or stop the skin penetration of sunscreen agents for the ultimate purposes of enhancing the bio-safety of sunscreen products.

In another aspect of the present invention, there is provided a formulation scheme using sunscreen agents bearing carboxyl function groups and excipients consisting of amine groups to reduce skin penetration of sunscreen agents or stop the skin penetration of sunscreen agents for the ultimate purposes of enhancing the bio-safety of sunscreen products.

In still another aspect of the present invention, there is provided a formulation scheme using sunscreen agents bearing amine function groups and the excipients consisting of carboxyl groups to reduce skin penetration of sunscreen agents or stop the skin penetration of sunscreen agents for the ultimate purposes of enhancing the bio-safety of sunscreen products.

EXAMPLES

The invention is illustrated herein by the experiments described by the following examples, which should not be considered as limiting. Those skilled in the art will understand that this invention may be embodied in many different forms and should not be constructed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Synthesis of Sunscreen Agent (4-Benzoyl-3-hydroxy-phenoxy)-acetic acid Synthesis scheme of (4-Benzoyl-3-hydroxy-phenoxy)-acetic acid

Synthesis of Intermediate 3

| Material | Molar Mass | Starting material | Equivalent |
| --- | --- | --- | --- |
| 1 | 110.11 | 10 g/0.09 mol | 1.0 |
| 2 | 140.57 | 12.77 g/0.09 mol | 1.0 |
| AlCl$_3$ | 133.34 | 14.53 g/0.11 mol | 1.2 |
| Chlorobenzene | | 75 ml | |

To a nitrogen-filled three-necked-flask 1,3-dihydroxy-benzene (10 g, 0.09 mol) and chlorobenzene (75 mL) were charged. Aluminum chloride (14.53 g, 0.11 mol) was added while stirring. Benzyl chloride was added to the above mixture drop wisely. After completing the addition, the temperature of the content was raised to 90° C. while stirring. The agitation was stopped when the compound 1,3-dihydroxy-benzene was used up with TLC (PE:EA=2:1)

When the temperature dropped to 50° C., dichloromethane (500 mL) and 1N sodium hydroxide (200 mL) were added. The mixture was stirred for 5 min. After settling, separate organic phase from aqueous phase. To the aqueous phase was added 1N hydrochloric acid until the pH reached pH=4. A huge amount of solids were precipitated. The solid was vacuum-filtered and washed with water until the filtrate is neutral. Drying in an oven, a yellowish solid product 2,4-dihydroxybenzophenone was obtained (18.90 g, 97.1%).

Synthesis of Intermediate 4

| Material | Molar Mass | Starting material | Equivalent |
| --- | --- | --- | --- |
| 2,4-dihydroxybenzo-phenone | 214.22 | 2.14 g/0.01 mol | 1.0 |
| 3A | 195.05 | 1.95 g/0.01 mol | 1.0 |
| Potassium carbonate | 183.21 | 5.49 g/0.03 mol | 3.0 |
| Potassium Iodide | 166.00 | 1.66 g/0.01 mol | 1.0 |
| 18-crown-6 | 264.32 | 2.64 g/0.01 mol | 1.0 |
| Acetone | | 100 ml | |

To a three-necked-flask containing 2,4-dihydroxy-benzophenone (2.14 g, 0.01 mol) and acetone (100 mL) were charged tert-butyl 2'-bromo-acetate (1.95 g, 0.01 mol), potassium carbonate (5.49 g, 0.03 mol), potassium iodide (1.66 g, 0.01 mol), and 18-crown-6 (2.64 g, 0.01 mol) while stirring. The mixture was stirred and heated until re-fluxing. Stopped the reaction when all 1,3-dihydroxy-benzophenone was consumed monitored with TLC (PE:EA=2:1). Let the temperature drop to ambient temperature. Filter under vacuum, the solids were washed with acetone. For filtrate the solvent was removed under vacuum completely. Via silicon column (PE:EA=20:1) Compound (4-Benzoyl-3-hydroxy-phenoxy)-acetic acid tert-butyl ester white solid was obtained (2.23 g, yield 72.9%)

Synthesis of (4-Benzoyl-3-hydroxy-phenoxy)-acetic acid

| Material | Molar Mass | Starting material | Equivalent |
|---|---|---|---|
| (4-Benzoyl-3-hydroxy-phenoxy)-acetic acid tert-butyl ester | 328.26 | 2 g/6.09 mmol | |
| Triflouroacetic acid | 114.02 | 10 ml | |
| Dichloromethane | | 20 ml | |

To a flask containing (4-benzoyl-3-hydroxy-phenoxy)-acetic acid tert-butyl ester (2 g, 6.09 mmol) and dichloromethane was added trifluoroacetic acid (10 mL, 130.6 mmol) while stirring. After Stirring for 3 hours (4-Benzoyl-3-hydroxy-phenoxy)-acetic acid tert-butyl ester disappeared based on TLC (PE:EA=3:1). Under vacuum trifluoroacetic acid was removed. The concentrate was dissolved in dichloromethane (150 mL). The organic phase was washed with 1N sodium hydroxide solution (50 mL). The aqueous phase was yellow in color. Under agitation 1N hydrochloric acid was added to the aqueous phase resulting in the formation of white precipitate and the final pH=7. Under vacuum filtrate and the solid was washed with water. Drying (4-Benzoyl-3-hydroxy-phenoxy)-acetic acid (1.34 g, 80.7%)

Example 2

Synthesis of Sunscreen Agent (4-Aminomethoxy-2-hydroxy-phenyl)-phenyl-methanone Synthesis scheme of (4-Aminomethoxy-2-hydroxy-phenyl)-phenyl-methanone Synthesis of Intermediate 3

-continued

3

| Material | Molar Mass | Starting material | Equivalent |
|---|---|---|---|
| 1,3-dihydroxy-benzene | 110.11 | 10 g/0.09 mol | 1.0 |
| Benzyl chloride | 140.57 | 2.77 g/0.09 mol | 1.0 |
| AlCl$_3$ | 133.34 | 14.53 g/0.11 mol | 1.2 |
| Chlorobenzene | | 75 ml | |

To a nitrogen-filled three-necked-flask 1,3-dihydroxy-benzene (10 g, 0.09 mol) and chlorobenzene (75 mL) were charged. Aluminum chloride (14.53 g, 0.11 mol) was added while stirring. Benzyl chloride was added to the above mixture drop wisely. After completing the addition, the temperature of the content was raised to 90° C. while stirring. The agitation was stopped when the compound 1,3-dihydroxy-benzene was used up monitored with TLC (PE:EA=2:1)

When the temperature was dropped to 50° C., dichloromethane (500 mL) and 1N sodium hydroxide (200 mL) were added. The mixture was stirred for 5 min. After settling, separate organic phase from aqueous phase. To the aqueous phase was added 1N hydrochloric acid until the pH reached pH=4. A huge amount of solids were precipitated. The solid was filtered under vacuum and washed with water until the filtrate is neutral. Drying in an oven, a yellowish solid product 2,4-dihydroxybenzophenone was obtained (18.90 g, 97.1%).

Synthesis of Intermediate 5

| Material | Molar Mass | Starting material | Equivalent |
|---|---|---|---|
| 2,4-dihydroxybenzophenone | 214.22 | 2.14 g/0.01 mol | 1.0 |
| 2-Bromomethyl-isoindole-1.3-dione | 240.06 | 2.40 g/0.01 mol | 1.0 |
| Potassium carbonate | 183.21 | 5.49 g/0.03 mol | 3.0 |
| DMF | | 30 mL | |

To a three-necked-flask containing 2,4-dihydroxy-benzophenone (2.14 g, 0.01 mol) and DMF (30 mL) were charged compound 2-Bromomethyl-isoindole-1.3-dione (2.40 g, 0.01 mol) and potassium carbonate (5.49 g, 0.03 mol) while stirring. The mixture was stirred and heated until refluxing. Stop the reaction when all 2,4-dihydroxy-benzophenone was used up monitored with TLC (PE:EA=2:1). The mixture was cooled down to room temperature. Filter under vacuum, the solids were washed with acetone. For filtrate the solvent was removed under vacuum completely. Via silicon column (PE:EA=20:1) Intermediate 5 was obtained as colorless solid (3.06 g, yield 81.9%)

Synthesis of (4-Aminomethoxy-2-hydroxy-phenyl)-phenyl-methanone

| Material | Molar Mass | Starting material | Equivalent |
|---|---|---|---|
| 5 | 373.36 | 2 g/5.35 mmol | 1 |
| Hydrazine | 50.06 | 0.6 mL | 2 |
| Ethanol | | 10 ml | |

To a 100 mL flask containing intermediate 5 (2 g, 5.35 mmol) and ethanol (10 mL) was added hydrazine (0.6 mL, 5.35×2 mmol) while stirring. The mixture was stirred for 3 hours at the temperature of re-fluxing and compound 5 disappeared based on TLC (PE:EA=2:1). Under vacuum ethanol was removed. The concentrate was dissolved in dichloromethane (50 mL). The organic phase was washed with saturated brine solution (20 mL). After separating the aqueous phase, the organic phase was dried over anhydrous sodium sulfate. The concentrated solution was subjected to silicate column purification. Yellowish solid of (4-Aminomethoxy-2-hydroxy-phenyl)-phenyl-methanone (0.78 g, yield 59.8%) was obtained.

Example 3

Benzoic Acid Formulation

Benzoic Acid Formulation Composition

| Benzoic Acid | Chitosan | Glycerol | Water |
|---|---|---|---|
| 260.84 mg | 0.51 g | 1.09 g | 15.39 g |

Add benzoic acid, chitosan polymer, and water to a beaker. Stir for 2 hours a solution was obtained. Add glycerol 1.09 g and mix thoroughly. Evaporate water at ambient temperature until reaching equilibrium. A transparent ointment (7.21 g) was obtained. Benzoic acid content is 3.6%.

Formulation Chemistry

Chitosan polymer contains —$NH_2$ amine groups. The N % is 8.695%. When mixed with benzoic acid, —$NH_2$ amine groups will react with benzoic acid to form benzoic anion and ammonium cation. Due to the ionic interaction between the chitosan and benzoic acid and the bulkiness of chitosan polymer the skin penetration of benzoic acid will be either dramatically reduced or eliminated.

Formulation Scheme of Benzoic Acid/Chitosan

Benzoic Acid Control Formulation

For the purpose of comparison, a benzoic acid control formulation was prepared. Lack of the above-mentioned ionic interaction between benzoic acid and excipient matrix is the base as a control standard. The composition is listed in the following table.

Control Formulation Composition for Benzoic Acid Formulation

| Benzoic Acid | PEG 400 | PEG 1500 |
|---|---|---|
| 1.01 g | 5.00 g | 4.00 g |

Weigh each component, benzoic acid, PEG 400 and PEG 1500, into a beaker. The mixture was heated in a 35° C. oven and was mixed thoroughly until a clear viscus solution was obtained. Cooling to room temperature yielded an ointment.

Mice Test Procedures:

1. Mice preparation and blood sample taking: 12 mice were fed with adequate food and water for 3 days. 12 hours before the test the food was removed and only water was given. The 12 mice were randomly divided into two groups. Two hours before the test the mice were subjected to anesthesia and the hair on the back (1.0-1.5 $cm^2$) was removed. After recovering from anesthesia one group of mice will be applied testing ointment sample while the other group will be applied with control standard sample. At 5, 15, 30, 60, 120 min. blood sample (1 mL) will be collected after removing the eyes.

2. Blood sample pretreatment: after the blood sample was taken, it was immediately subjected to centrifugation 10 min. at 12000 rpm, supernatant plasma layer was taken, preserved at −20° C. for later use.

3. Blood sample preparation: Accurately transfer 150 μL plasma sample to a 1.5 mL EP test tube. Add methanol and acetonitrile 200 μL, respectively. Vertex mix for 1 min., then centrifuge for 10 min. at 12000 rpm. Precisely transfer the supernatant solution to another test tube. At 40° C. blow $N_2$ through to dryness. To the solids left add methanol 150 μL, vertex mix for 1 min. centrifuge at 12000 rpm for 10 min. Supernatant solution was used directly for HPLC analysis.

4. HPLC analysis: Column: C18 RP column (250×4.6 mm, 5 μm); column temperature: 25° C.; mobile phase: MeOH:0.1% $H_3PO_4$=45:55; Flow rate: 1.0 mL/min.; Wavelength: 228 nm; Injection volume: 10 μL Example 4

4-Methoxy-benzylamine Formulation

4-Methoxy-benzylamine Formulation Composition

| 4-Methoxy-benzylamine | Hyaluronic acid | PEG 400 | Water |
|---|---|---|---|
| 0.50 g | 1.71 g | 2.00 g | 4.72 |

Mix 4-methoxy-benzylamine (0.50 g) with PEG 400 (1.01 g). Add the mixture to the hyaluronic acid water solution (7.5%) while stirring. Evaporate water in an oven at 40° C. Add PEG 400 (0.99 g) to the mixture. Evaporate water in an oven at 40° C. until reaching equilibrium. An ointment (8.93 g) was obtained. The content of 4-Methoxy-benzylamine is 5.5%.

Formulation Chemistry

Hyaluronic acid is a polysaccharide polymer with carboxyl groups. The molar % of carboxyl group is 50.0%. When mixed with 4-methoxy-benzylamine, —$NH_2$ amine groups will react with carboxyl groups to form carboxyl anion and ammonium cation. Due to the ionic interaction between the hyaluronic polymer and 4-methoxy-benzylamine, and the bulkiness of hyaluronic polymer, the skin penetration of 4-methoxy-benzylamine through into blood circulation system will be either dramatically reduced or completely eliminated.

Formulation Scheme of 4-Methoxy-benzylamine-/Hyaluronic Acid

-continued

4-Methoxy-benzylamine Control Formulation

For the purpose of comparison, a 4-methoxy-benzylamine control formulation was prepared. Lack of the above-mentioned ionic interaction between 4-methoxy-benzylamine and the excipient matrix is the base as a control standard. The composition is listed in the following table.

4-Methoxy-benzylamine Control Formulation Composition

| 4-methoxy-benzylamine | PEG 400 | PEG 1500 |
|---|---|---|
| 0.50 g | 5.56 g | 3.87 g |

Weigh PEG 400 and PEG 1500 into a beaker. The beaker was placed in a 35° C. oven. Mix until a clear solution was obtained. Weigh 4-methoxy-benzylamine into the container containing PEG 400 and PEG 1500. Mix thoroughly. A clear ointment was obtained at ambient temperature.

Mice Test Procedures:
1. Mice preparation and blood sample taking: 12 mice were fed with adequate food and water for 3 days. 12 hours before the test the food was removed and only water was given. The 12 mice were randomly divided into two groups. Two hours before the test the mice were subjected to anesthesia and the hair on the back (1.0-1.5 cm$^2$) was removed. After recovering from anesthesia one group of mice will be applied testing ointment sample while the other group will be applied with control standard sample. At 5, 15, 30, 60, 120 min. blood sample (1 mL) will be collected after removing the eyes.
2. Blood sample pretreatment: after the blood sample was taken, it was immediately subjected to centrifugation 10 min. at 12000 rpm, supernatant plasma layer was taken, preserved at −20° C. for later use.
3. Blood sample preparation: Accurately transfer 150 µL plasma sample to a 1.5 mL EP test tube. Add methanol and acetonitrile 200 µL, respectively. Vertex mix for 1 min., then centrifuge for 10 min. at 12000 rpm. Precisely transfer the supernatant solution to another test tube. At 40° C. blow N$_2$ through to dryness. To the solids left add methanol 150 µL, vertex mix for 1 min. centrifuge at 12000 rpm for 10 min. Supernatant solution was used directly for HPLC analysis.
4. HPLC analysis: Column: C18 RP column (250×4.6 mm, 5 µm); column temperature: 25° C.; mobile phase: ACN:H$_2$O=60:40; Flow rate: 1.0 mL/min.; Wavelength: 254 nm; Injection volume: 20 µL;

Example 5

(4-Benzoyl-3-hydroxy-phenoxy)-acetic Acid Formulation (4-Benzoyl-3-hydroxy-phenoxy)-acetic Acid Formulation Composition

| (4-Benzoyl-3-hydroxy-phenoxy)-acetic acid | Polyethyleneimine | PEG 400 | PEG 1500 |
|---|---|---|---|
| 110.85 mg | 261.97 mg | 262.55 mg | 235.44 mg |

Dissolve polyethyleneimine (261.97 mg) in water (688.45 mg). Mix (4-Benzoyl-3-hydroxy-phenoxy)-acetic acid (110.85 mg) with polyethyleneimine water solution prepared above. Add PEG 400 and PEG 1500 to the mixture while mixing. Raise temperature to 35° C. and keep mixing until a clear yellowish ointment (1.07 g) was obtained. The content of (4-Benzoyl-3-hydroxy-phenoxy)-acetic acid is 10.36%.

Formulation Chemistry (4-Benzoyl-3-hydroxy-phenoxy)-acetic acid contains carboxyl group. When mixed with polyethyleneimine, —NH$_2$ amine groups will react with carboxyl groups to form carboxyl anion and ammonium cation. Due to the ionic interaction and the formation of polyethyleneiminium multiple carbonate, (4-Benzoyl-3-hydroxy-phenoxy)-acetic acid moieties were locked in the matrix. The diffusion of the active UV ray blocking agent through skin into blood circulation system will be either dramatically reduced or completely eliminated.

Formulation Scheme of (4-Benzoyl-3-hydroxy-phenoxy)-acetic acid/Polyethyleneimine (4-Benzoyl-3-hydroxy-phenoxy)-acetic Acid
Control Formulation For the purpose of comparison, 2-Hydroxy-4-methoxy-benzophenone (oxybenzophenone) was chosen to be the standard for (4-Benzoyl-3-hydroxy-phenoxy)-acetic acid. Lack of above-mentioned interaction between the active UV ray blocking agent and the excipient matrix is the base as a control standard. The composition is listed in the following table.

2-Hydroxy-4-methoxybenzophenone Control
Formulation Composition

| 2-Hydroxy-4-methoxybenzophenone | PEG 400 | PEG 1500 |
|---|---|---|
| 207.20 mg | 1001.80 mg | 754.04 mg |

Weigh PEG 400 and PEG 1500 into a beaker. The beaker was placed in a 35° C. oven. Mix until a clear solution was obtained. Weigh 2-Hydroxy-4-methoxybenzophenone into the container containing PEG 400 and PEG 1500. Mix thoroughly. A clear ointment was obtained.

Mice Test Procedures:

1. Mice preparation and blood sample taking: Twenty mice were fed with adequate food and water for 3 days. Twelve hours before the test the food was removed and only water was given. The 20 mice were randomly divided into two groups. Two hours before the test the mice were subjected to anesthesia and the hair on the back (2.0-2.5 cm$^2$) was removed. After recovering from anesthesia one group of mice will be applied testing ointment sample while the other group will be applied with control standard sample. At 5, 15, 30, 60, 120 min. blood sample (1 mL) will be collected after removing the eyes.

2. Blood sample pretreatment: after the blood sample was taken, it was immediately subjected to centrifugation 10 min. at 12000 rpm, supernatant plasma layer was taken, preserved at −20° C. for later use.

3. Blood sample preparation: Accurately transfer 150 μL plasma sample to a 1.5 mL EP test tube. Add methanol and acetonitrile 200 μL, respectively. Vertex mix for 1 min., then centrifuge for 10 min. at 12000 rpm. Precisely transfer the supernatant solution to another test tube. At 40° C. blow $N_2$ through to dryness. To the solids left add methanol 150 μL, vertex mix for 1 min. centrifuge at 12000 rpm for 10 min. Supernatant solution was used directly for HPLC analysis.

4. HPLC analysis:

(4-Benzoyl-3-hydroxy-phenoxy)-acetic acid: Column: C18 RP column (250×4.6 mm, 5 μm); column temperature: 25° C.; mobile phase:
MeOH:0.14% $H_3PO_4$=65:35; Flow rate: 1.0 mL/min.; Wavelength: 290 nm; Injection volume: 20 μL;

2-Hydroxy-4-methoxybenzophenone: Column: C18 RP column (250×4.6 mm, 5 m); column temperature: 25° C.; Mobile phase: MeOH:$H_2O$=80:20; Flow rate: 1.0 mL/min.; Wavelength: 290 nm; Injection volume: 20 μL;

Example 6

(4-Aminomethoxy-2-hydroxy-phenyl)-phenyl-methanone
Formulation (4-Aminomethoxy-2-hydroxy-phenyl)-phenyl-methanone
Formulation Composition

| (4-Aminomethoxy-2-hydroxy-phenyl)-phenyl-methanone | Glutaric acid | PEG 200 | PEG 1500 |
|---|---|---|---|
| 112.22 mg | 31.35 mg | 542.07 mg | 388.21 mg |

Mix PEG 200 (542.07 mg) and PEG 1500 (388.21 mg) while heating gently until a homogenous clear solution obtained. Dissolve glutaric acid (31.35 mg) in PEG 200/PEG 1500 solution (388.27 mg). Dissolve (4-Aminomethoxy-2-hydroxy-phenyl)-phenyl-methanone (112.22 mg) in PEG 200/PEG 1500 solution (542.01 mg) prepared above. Mixing the two solutions yielded a clear yellowish ointment (1.07 g). The content of (4-Aminomethoxy-2-hydroxy-phenyl)-phenyl-methanone is 10.5%.

Formulation Chemistry (4-Aminomethoxy-2-hydroxy-phenyl)-phenyl-methanone contains —$NH_2$ amino groups. When mixed with glutaric acid, $NH_2$ amine groups of the active sun screen agent will react with carboxyl groups to form carboxyl anion and ammonium cation. Due to the ionic interaction and the formation of glutaric di-carbonate, the diffusion of (4-Aminomethoxy-2-hydroxy-phenyl)-phenyl-methanone moieties, the active UV ray blocking agent, through skin into blood circulation system will be either dramatically reduced or completely eliminated.

Formulation Scheme of (4-Aminomethoxy-2-hydroxy-phenyl)-phenyl-methanone/Glutaric Acid (4-Aminomethoxy-2-hydroxy-phenyl)-phenyl-methanone Control Formulation For the purpose of comparison, 2-Hydroxy-4-methoxybenzophenone was selected as standard. Lack of above-mentioned interaction between the active UV ray blocking agent and the excipient matrix fulfil the purpose of a control standard. The composition is listed in the following table.

2-Hydroxy-4-methoxybenzophenone Control Formulation Composition

| 2-Hydroxy-4-methoxybenzophenone | PEG 400 | PEG 1500 |
|---|---|---|
| 207.20 mg | 1001.80 mg | 754.04 mg |

Weigh PEG 400 and PEG 1500 into a beaker. The container was placed in a 35° C. oven. Mix until a clear solution was obtained. Weigh for 2-Hydroxy-4-methoxybenzophenone into the container containing PEG. Mix thoroughly. A clear solution was obtained Mice Test Procedures:
1. Mice preparation and blood sample taking: Twelve mice were fed with adequate food and water for 3 days. Twelve hours before the test the food was removed and only water was given. The 12 mice were randomly divided into two groups. 2 hours before the test the mice were subjected to anesthesia and the hair on the back (2.0-2.5 cm²) was removed. After recovering from anesthesia one group of mice will be applied testing ointment sample while the other group will be applied with control standard sample. At 5, 15, 30, 60, 120 min. blood sample (1 mL) will be collected after removing the eyes.
2. Blood sample pretreatment: after the blood sample was taken, it was immediately subjected to centrifugation 10 min. at 12000 rpm, supernatant plasma layer was taken, preserved at −20° C. for later use.
3. Blood sample preparation: Accurately transfer 150 µL plasma sample to a 1.5 mL EP test tube. Add methanol and acetonitrile 200 µL, respectively. Vertex mix for 1 min., then centrifuge for 10 min. at 12000 rpm. Precisely transfer the supernatant solution to another test tube. At 40° C. blow $N_2$ through to dryness. To the solids left add methanol 150 µL, vertex mix for 1 min. centrifuge at 12000 rpm for 10 min. Supernatant solution was used directly for HPLC analysis.
4. HPLC analysis:
   (4-Aminomethoxy-2-hydroxy-phenyl)-phenyl-methanone: Column: C18 RP column (250×4.6 mm, 5 µm); column temperature: 25° C.; mobile phase: MeOH: 0.14% $H_3PO_4$=65:35; Flow rate: 1.0 mL/min.; Wavelength: 290 nm; Injection volume: 20 µL;
   2-Hydroxy-4-methoxybenzophenone: Column: C18 RP column (250×4.6 mm, 5 µm); column temperature: 25° C.: Mobile phase: MeOH:$H_2O$=80:20; Flow rate: 1.0 mL/min.; Wavelength: 290 nm; Injection volume: 20 µL;

Example 7

Oxybenzone Formulation

2-Hydroxy-4-methoxybenzophenone Formulation Composition

| 2-Hydroxy-4-methoxybenzophenone | Polyethylenimine | PEG 200 | PEG 1500 |
|---|---|---|---|
| 101.67 mg | 79.04 mg | 509.98 mg | 339.09 mg |

Mix PEG 200 (509.98 mg) and PEG 1500 (339.09 mg) while heating gently until a homogeneous clear solution obtained. Dissolve 2-Hydroxy-4-methoxybenzophenone (101.67 mg) in PEG 200/PEG 1500 solution. Adding polyethyleneimine (PEI) (79.04 mg) yielded a clear yellowish ointment (1.03 g). The content of 2-Hydroxy-4-methoxybenzophenone is 9.9%.

Formulation Chemistry

The proton of the hydroxyl group of 2-hydroxy-4-methoxybenzophenone is somewhat acidic. The $-NH_2$ amine groups of excipient polyethyleneimine will react with 2-Hydroxy-4-methoxybenzophenone to form an anion and ammonium cation. Due to the ionic interaction, the penetration of 2-Hydroxy-4-methoxybenzophenone moieties, the active UV ray blocking agent, through skin barrier into blood circulation system will be either dramatically reduced or eliminated.

Formulation Scheme of Oxybenzophenone/Polyethyleneimine

2-Hydroxy-4-methoxybenzophenone Control Formulation Composition

| 2-Hydroxy-4-methoxybenzophenone | PEG 400 | PEG 1500 |
|---|---|---|
| 207.20 mg | 1001.80 mg | 754.04 mg |

Weigh PEG 400 and PEG 1500 into a beaker. The beaker was placed in a 35° C. oven. Mix until a clear solution was obtained. Weigh for 2-Hydroxy-4-methoxybenzophenone into the container containing PEG. Mix thoroughly. A clear ointment was obtained.

Mice Test Procedures:
1. Mice preparation and blood sample taking: Thirty mice were fed with adequate food and water for 3 days. Twelve hours before the test the food was removed and only water was given. These 30 mice were randomly divided into two groups. Two hours before the test the mice were subjected to anesthesia and the hair on the back (2.0-2.5 cm$^2$) was removed. After recovering from anesthesia one group of mice will be applied testing ointment sample while the other group will be applied with control standard sample. At 5, 15, 30, 60, 90, 120 min. blood sample (1 mL) will be collected after removing the eyes.
2. Blood sample pretreatment: after the blood sample was taken, it was immediately subjected to centrifugation 10 min. at 12000 rpm, supernatant plasma layer was taken, preserved at −20° C. for later use.
3. Blood sample preparation: Accurately transfer 150 μL plasma sample to a 1.5 mL EP test tube. Add methanol and acetonitrile 200 μL, respectively. Vertex mix for 1 min., then centrifuge for 10 min. at 12000 rpm. Precisely transfer the supernatant solution to another test tube. At 40° C. blow $N_2$ through to dryness. To the solids left add methanol 150 μL, vertex mix for 1 min. centrifuge at 12000 rpm for 10 min. Supernatant solution was used directly for HPLC analysis.
4. HPLC analysis:
   2-Hydroxy-4-methoxybenzophenone: Column: C18 RP column (250×4.6 mm, 5 μm); column temperature: 25° C.; Mobile phase: MeOH:$H_2O$=80:20; Flow rate: 1.0 mL/min.; Wavelength: 290 nm; Injection volume: 20 μL;

Example 8

Avobenzone Formulation

Avobenzone Formulation Composition

| Avobenzone | Polyethylenimine | PEG 200 | PEG 1500 |
|---|---|---|---|
| 104.78 mg | 102.17 mg | 1109.95 mg | 735.90 mg |

Mix PEG 200 (1109.95 mg) and PEG 1500 (735.90 mg) while heating gently until a homogenous clear solution obtained. Dissolve avobenzone (104.78 mg) in PEG 200/PEG 1500 solution. Adding polyethyleneimine (102.17 mg) yielded a clear yellowish ointment (2.05 g). The content of 2-Hydroxy-4-methoxybenzophenone is 5.1%.

Formulation Chemistry

Avobenzone exists in enol form and beta di-ketone form. Enol form is energetically favorable than di-ketone form. The proton of the hydroxyl group of enol form is somewhat acidic. The $NH_2$ amine groups of excipient polyethyleneimine (PEI) will react with the active proton to form enol anion and ammonium cation. Due to the ionic interaction, the penetration of avobenzone moieties, the active UV ray blocking agent, through skin into blood circulation system will be either dramatically reduced or completely eliminated.

Avobenzone Control Formulation

| Avobenzone | Iso-Propanol | PEG 200 | PEG 1500 |
|---|---|---|---|
| 101.51 mg | 104.92 mg | 1130.46 mg | 742.77 mg |

Weigh PEG 200 and PEG 1500 into a beaker. The beaker was placed in a 35° C. oven. Mix until a clear solution was obtained. Weigh avobenzone into the container containing PEG. Mix thoroughly. A clear ointment was obtained.

Mice Test Procedures:
1. Mice preparation and blood sample taking: Thirty mice were fed with adequate food and water for 3 days. Twelve hours before the test the food was removed and only water was given. Twenty-four mice were randomly divided into two groups. Two hours before the test the mice were subjected to anesthesia and the hair on the back (2.0-2.5 cm$^2$) was removed. After recovering from anesthesia one group of mice will be applied testing ointment sample while the other group will be applied with control standard sample. At 5, 15, 30, 60, 90, 120 min. blood sample (1 mL) will be collected after removing the eyes.
2. Blood sample pretreatment: after the blood sample was taken, it was immediately subjected to centrifugation 10 min. at 12000 rpm, supernatant plasma layer was taken, preserved at −20° C. for later use.

3. Blood sample preparation: Accurately transfer 150 μL plasma sample to a 1.5 mL EP test tube. Add methanol and acetonitrile 200 μL, respectively. Vertex mix for 1 min., then centrifuge for 10 min. at 12000 rpm. Precisely transfer the supernatant solution to another test tube. At 40° C. blow $N_2$ through to dryness. To the solids left add methanol 150 μL, vertex mix for 1 min. centrifuge at 12000 rpm for 10 min. Supernatant solution was used directly for HPLC analysis.

4. HPLC analysis:

Avobenzone: Column: C18 RP column (250×4.6 mm, 5 μm); column temperature: 25° C.; mobile phase: MeOH:$H_2O$=90:10; Flow rate: 1.0 mL/min.; Wavelength: 360 nm; Injection volume: 20 μL;

Example 9

Benzoic Acid Formulation Mice Skin Penetration Test Results

Figure 1:
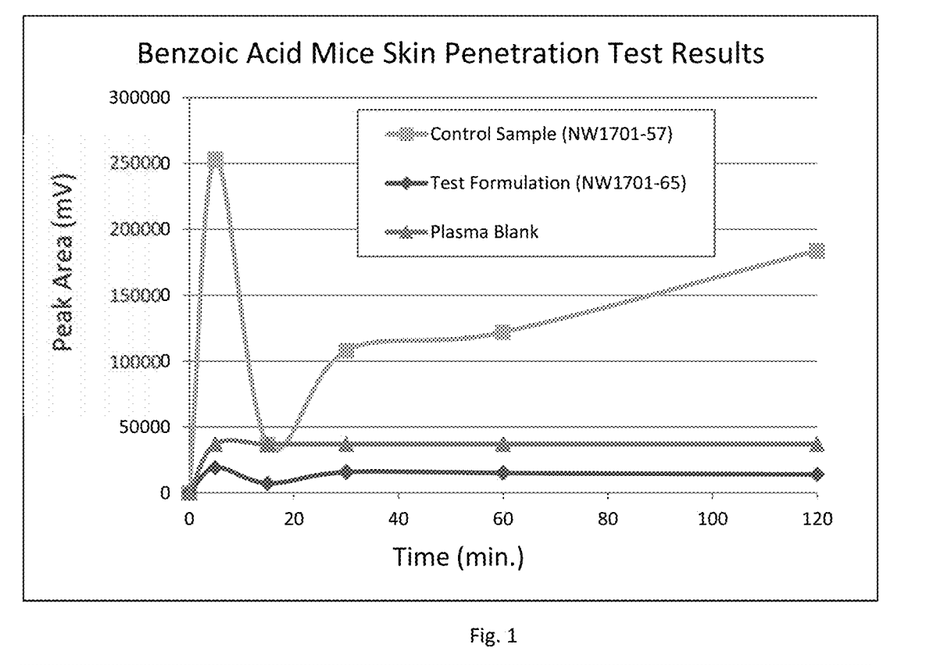
FIG. 1 shows benzoic acid mice skin penetration test results in connection with a formulation based on Example 3 of the present application.

As shown in FIG. 1, the concentration of benzoic acid in the blood sample for control formulation are significantly higher than the concentrations of benzoic acid for the test formulation samples at each time point, respectively. The area under curve (AUC), representing the exposure of the benzoic acid, for the control sample is 8.9 times of the AUC of the test formulation, revealing the success of the present formulation scheme.

Example 10

4-Methoxy-benzylamine Formulation Mice Skin Penetration Test Results

Figure 2:
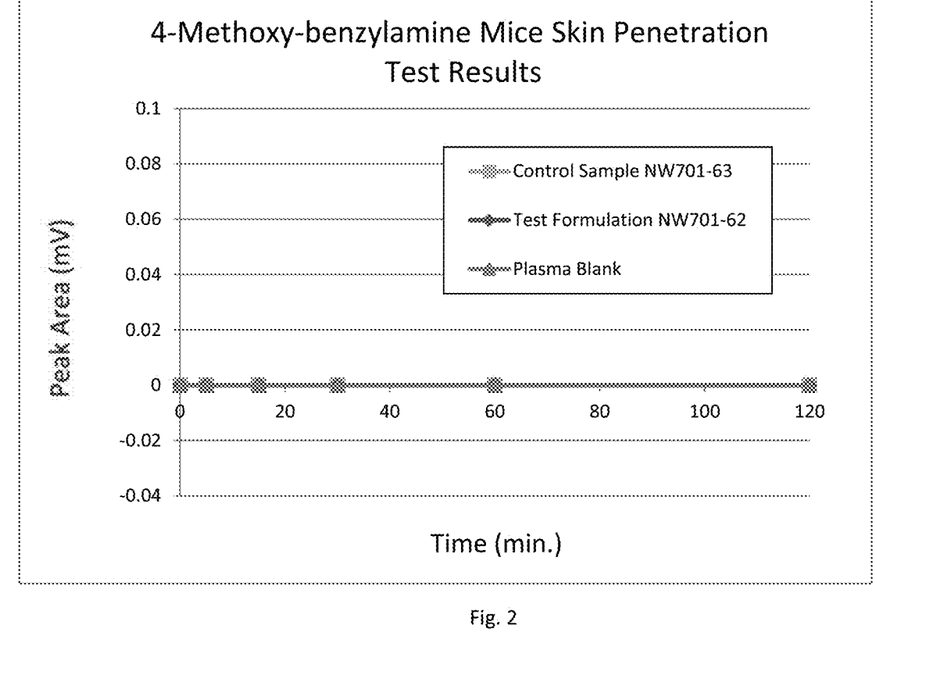
FIG. 2 shows 4-methoxy-benzylamine mice skin penetration test results in connection with a formulation based on Example 4 of the present application.

As shown in FIG. 2, no sunscreen agent, 4-methoxy-benzylamine, was detected in all test samples, plasma blank sample, and the control samples, indicating 4-methoxy-benzylamine could not penetrate the skin of mice.

Example 11

Figure 3:
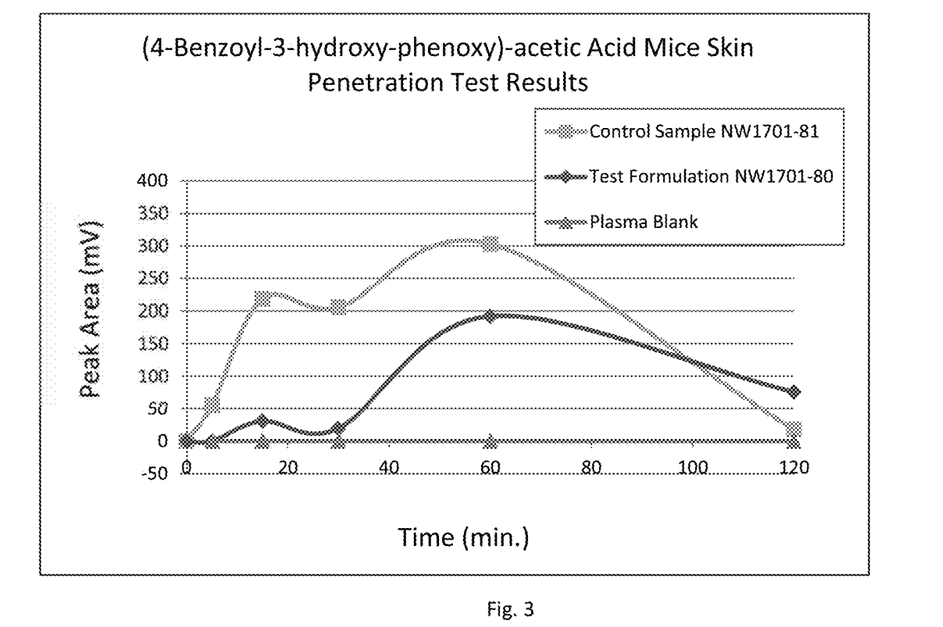
FIG. 3 shows (4-benzoyl-3-hydroxy-phenoxy)-acetic acid mice skin penetration test results in connection with a formulation based on Example 5 of the present application.

(4-Benzoyl-3-hydroxy-phenoxy)-acetic Acid Formulation Mice Skin Penetration Test Results At the initial 30 min. the skin penetration rate of sunscreen agent was minimal. As shown in FIG. 3, overall the AUC of control sample is 1.8 times of AUC of the present formulation, reducing the exposure of sunscreen agent by 45% vs. control sample.

Example 12

Figure 4:
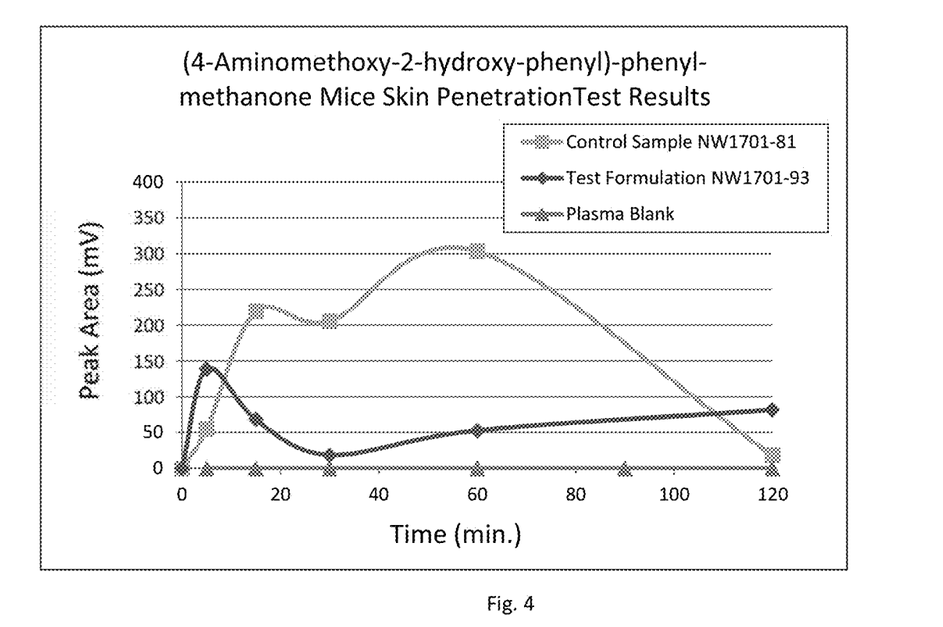
FIG. 4 shows (4-aminomethoxy-2-hydroxy-phenyl)-phenyl-methanone mice skin penetration test results in connection with a formulation based on Example 6 of the present application.

(4-Aminomethoxy-2-hydroxy-phenyl)-phenyl-methanone Formulation Mice Skin Penetration Test Results As shown in FIG. 4, except the 5 min. time point the exposure of active sunscreen agent for the test sample is generally lower compared to that of the control sample. The AUC, sunscreen agent exposure, for control sample is 3.0 times more than that for the (4-Aminomethoxy-2-hydroxy-phenyl)-phenyl-methanone test formulation. In another word the formulation of the present invention reduced the sunscreen agent exposure by 60% vs. the standard control formulation.

Example 13

Oxybenzone+PEI Formulation Mice Skin Penetration Test Results

Figure 5:
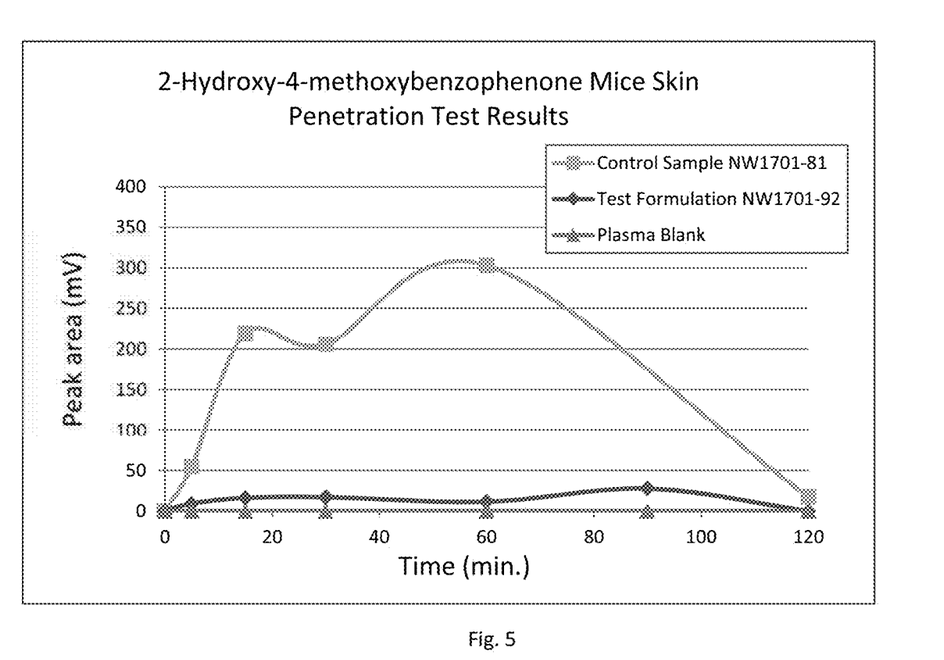
FIG. 5 shows 2-hydroxy-4-methoxybenzophenone (oxybenzone) mice skin penetration test results in connection with a formulation based on Example 7 of the present application.

As shown in FIG. 5, with regards to all sampling time points the active sunscreen agent exposure for oxybenzone formulation is consistently lower than that for the control sample. The AUC of the control formulation is 10 times of the AUC of the test formulation of the present invention, decreasing oxybenzone exposure by 90% compared to the standard control formulation.

Example 14

Avobenzone+PEI Formulation Mice Skin Penetration Test Results

Figure 6:
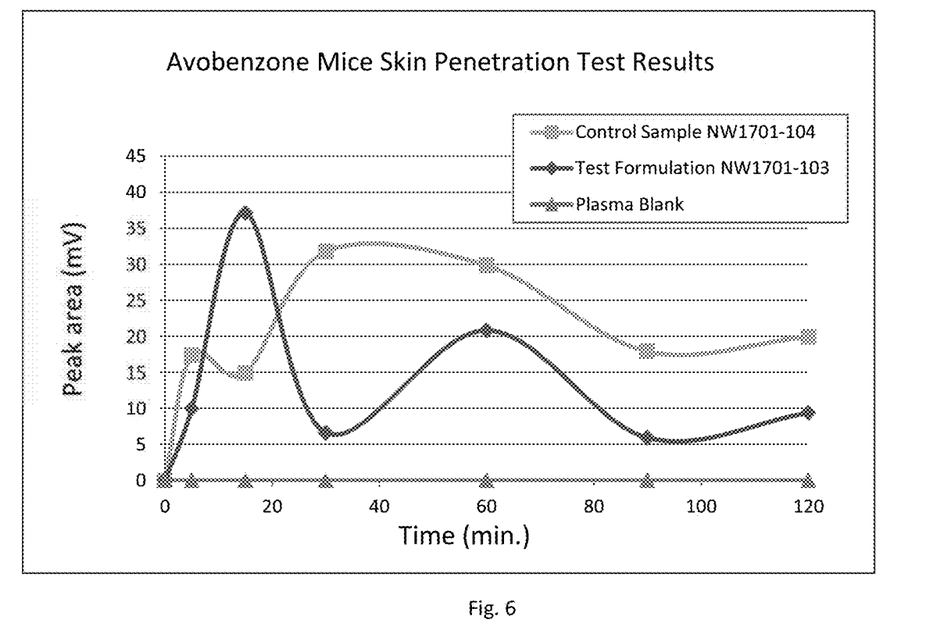
FIG. 6 shows avobenzone formulation mice skin penetration test results in connection with a formulation based on Example 8 of the present application.

As shown in FIG. 6, except the sampling time point of 15 min., the active sunscreen agent exposure for the avobenzone formulation is consistently lower than that for control sample. The exposure of control sample is 1.71 times of the test sample.

The invention is not limited by the embodiments described above which are presented as examples only but can be modified in various ways within the scope of protection defined by the appended patent claims.

What is claimed is:

1. A sunscreen formulation comprising:
   (1) an ionic complex that is formed between a compound A and an excipient B; and
   (2) an aqueous based carrier for topical administration, wherein the compound A is a sunscreen compound in enol form or with an active acidic proton or derivatized with —[$CH_2$]$_n$COOH or —[$CH_2$]$_n$$NH_2$, wherein n is 0 to 18; wherein the excipient B contains an amine functional group when the sunscreen compound is in enol form or with an active acidic proton or derivatized with —[$CH_2$]$_n$COOH, and/or wherein the excipient B contains a carboxyl functional group when the sunscreen compound is derivatized with —[$CH_2$]$_n$$NH_2$; and wherein the formulation is substantially free of the compound A in a free form.

2. The formulation of claim 1 comprising less than 20% molar equivalent of the compound A in free form relative to the molar amount of the ionic complex.

3. The formulation of claim 1 being free of a compound that is substantially detrimental to formation or existence of the ionic complex or the stability of the formulation.

4. The formulation of claim 3 wherein the compound that is substantially detrimental to formation or existence of the ionic complex or the stability of the formulation is another ionic compound that has not been recited in claim 1.

5. The formulation of claim 3 wherein the compound that is substantially detrimental to formation or existence of the ionic complex or the stability of the formulation is an ionic surfactant.

6. The formulation of claim 1 wherein the sunscreen compound to be derivatized with [$CH_2$]$_n$COOH is selected from the group consisting of avobenzone, cinoxate, dioxybenzone, homosalate, octocrylene, octyl methoxycinnamate, octyl salicylate, oxybenzone, and combinations thereof, and the derivatized sunscreen compound has the following structure:

7. The formulation of claim 6 wherein the derivatized sunscreen compound is (4-benzoyl-3-hydroxy-phenoxy)-acetic acid of the following formula:

8. The formulation of claim 1 wherein the sunscreen compound to be derivatized with —[CH$_2$]$_n$NH$_2$ is selected from the group consisting of avobenzone, cinoxate, dioxybenzone, homosalate, octocrylene, octyl methoxycinnamate, octyl salicylate, oxybenzone, and combinations thereof, and the derivatized sunscreen compound has the following structure:

9. The formulation of claim 8 wherein the derivatized sunscreen compound is (4-benzoyl-3-hydroxy-phenoxy)-acetic acid of the following formula:

10. The formulation of claim 1 wherein the excipient B that contains the amine functional group is selected from the group consisting of spermidine, spermine, tris-(2-aminoethyl)amine, 1,1,1-tris(aminomethyl)ethane, cyclen, polyvinylamine, polyallylamine, polyethyleneimine, chitosan, and combinations thereof.

11. The formulation of claim 1 wherein the excipient B that contains the carboxyl function group is selected from the group consisting of oxalic acid, malonic acid, succinic acid, glutaric acid, adipic acid, citric acid, isocitric acid, propane-1,2,3-tricarboxylic acid, carboxymethyl cellulose, polyacrylic acid, hyaluronic acid, and combinations thereof.

12. The formulation of claim 1 wherein the sunscreen compound in enol form is avobenzone.

13. The formulation of claim 1 wherein the sunscreen compound with the active acidic proton is selected from the group consisting of oxybenzone, diethylamino hydroxybenzoyl hexyl benzoate, homosalate, dioxybenzone, 2-ethylhexyl salicylate, sulisobenzone, and combinations thereof.

14. The formulation of claim 1 wherein the aqueous based carrier is selected from the group consisting of aqueous based chitosan, aqueous based hyaluronic acid, aqueous based PEG200, aqueous based PEG400, aqueous based PEG1500, and combinations thereof.

15. The formulation of claim 1 wherein the formulation is homogeneously transparent.

16. The formulation of claim 1 wherein the formulation is in form of an ointment or a viscus solution.

17. A method for protecting skin from ultraviolet radiation comprising applying the formulation of claim 1 to the skin in need thereof.

18. A method of making the formulation of claim 1 comprising:
dissolving the compound A in the carrier, reacting with the excipient B, and blending to form the formulation at a temperature range from 20° C. to 50° C.

19. The method of claim 18 comprising, prior to the step of blending, a step of making the compound A by derivatizing the sunscreen compound with —[CH$_2$]$_n$COOH or —[CH$_2$]$_n$NH$_2$, wherein n is 0 to 18.

20. (4-aminomethoxy-2-hydroxy-phenyl) phenyl-methanone of the following formula:

* * * * *